(12) United States Patent
Tuch

(10) Patent No.: US 6,303,644 B1
(45) Date of Patent: Oct. 16, 2001

(54) PROTON PUMP INHIBITOR IN THERAPEUTIC COMBINATION WITH ANTIBACTERIAL SUBSTANCES

(75) Inventor: Klaus Tuch, Ahrensburg (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/463,390

(22) PCT Filed: Jul. 21, 1998

(86) PCT No.: PCT/EP98/04553

§ 371 Date: Jan. 27, 2000

§ 102(e) Date: Jan. 27, 2000

(87) PCT Pub. No.: WO99/04816

PCT Pub. Date: Feb. 4, 1999

(30) Foreign Application Priority Data

Jul. 25, 1997 (EP) .................................................. 97112795

(51) Int. Cl.⁷ ........................ A61K 31/415; A61K 31/70; A61K 31/65; A61K 31/43; A61K 31/545
(52) U.S. Cl. ............................ 514/393; 514/24; 514/152; 514/199; 514/200; 514/394
(58) Field of Search .................................... 514/393, 394, 514/199, 200, 152, 24

(56) References Cited

U.S. PATENT DOCUMENTS

| | | | | |
|---|---|---|---|---|
| 5,629,305 | * | 5/1997 | Eek et al. ............................. | 514/199 |
| 5,945,124 | * | 8/1999 | Sachs et al. ......................... | 424/472 |
| 6,134,344 | * | 10/2000 | Depui et al. ........................ | 424/470 |

FOREIGN PATENT DOCUMENTS

| | | |
|---|---|---|
| 35 31 487 | 3/1986 | (DE) . |
| 0 005 129 | 10/1979 | (EP) . |
| 0 166 287 | 1/1986 | (EP) . |
| 0 174 726 | 3/1986 | (EP) . |
| 0 268 956 | 6/1988 | (EP) . |
| 0 434 999 | 7/1991 | (EP) . |
| 0 544 760 | 6/1993 | (EP) . |
| 92/03135 | * 3/1992 | (WO) . |
| 93/12817 | 7/1993 | (WO) . |
| 94/07490 | 4/1994 | (WO) . |
| 97/02021 | 1/1997 | (WO) . |

OTHER PUBLICATIONS

Windholz et al., The Merck Index., Tenth Edition, (1983) p. 83, reference No. 600 (amoxicillin).*
Hirai et al., "A Proton Pump Inhibitor, E3810, Has Antibacterial Activity Through Binding to Helicobacter Pylori", Journal of Gastroenterology, 1995; 30:461–464.
Murakami et al., "Atopic Dermatitis Successfully Treated by Eradication of Helicobacter Pylori", J Gastroenterol, Nov. 1996, 31 Suppl 9 P77–82.
Jonkers et al., "Omeprazole Inhibits Growth of Gram–Positive and Gram–Negative Bacteria Including Helicobacter Pylori in Vitro", J Antimicrob Chemother, Jan 1996, 37 (1), P145–50.
Greco et al., "Glossitis, Stomatitis, and Black Tongue With Lansoprazole Plus Clarithromycin and Other Antibiotics (1)" Annals of Pharmacotherapy, 1997, 31/12, (1548).
Kalas et al., "Connection Between Helicobacter Pylori Infection and Chronic Gastrointestinal Urticarial", Orv Hetil, Sep. 8, 1996, 137 (36), P1969–72.
Reinauer et al., "Schonlein–Henoch Purpura Associated With Gastric Helicobacter Pylori Infection", J Am Acad Dermatol, 11/95, 33 (5 PT 2) P876–9.
Malfertheiner, "Current European Concepts in the Management of Helicobacter Pylori Infection. The Maastricht Concensus Report", Gut, 1997, 41/1 (8–13).
Sachs, "Proton Pump Inhibitors and Acid–Related Diseases", Pharmacotherapy, 1997, 17/1 (22–37).
Kuipers et al., "Athrophic Gastritis and Helicobacter Pylori Infection in Patients with Reflux Esophagitis Treated With Omeprazole or Fundoaplication", New England Journal of Medicine, BD. 334, NR. 16, Apr. 18, 1996.

* cited by examiner

Primary Examiner—Kevin E. Weddington
(74) Attorney, Agent, or Firm—Jacobson Holman, PLLC

(57) ABSTRACT

The invention relates to the use of proton pump inhibitors as combination therapeutics in the treatment of bacterial diseases which do not affect the gastrointestinal track using antibacterially active compounds.

20 Claims, No Drawings

PROTON PUMP INHIBITOR IN THERAPEUTIC COMBINATION WITH ANTIBACTERIAL SUBSTANCES

FIELD OF APPLICATION OF THE INVENTION

The invention relates to the use of proton pump inhibitors as combination therapeutics in the treatment of bacterial diseases which do not affect the gastrointestinal tract using antibacterially active compounds.

KNOWN TECHNICAL BACKGROUND

A large number of patent applications and patents describe variously substituted 2-(2-pyridinylmethylsulfinyl)-1H-benzimidazoles, This class of compound is able to specifically inhibit gastric acid production and is therefore also described as the proton pump Inhibitors class. A whole series of proton pump inhibitors are in an advanced stage of clinical testing or already on the market. The following compounds, designated by the INN, which may be mentioned as examples are: omeprazole (EP-B 005 129), pantoprazole (EP-B 168 287), lansoprazole (EP-B 174 726), rabeprazole (EP-B 268 956), lemninoprazole (DE-A 35 31 487) and nepaprazole (EP-A 434 999).

European Patent 166 287, in which, inter alia, the compound pantoprazole (INN) is patented, states that the compounds according to the invention are suitable for the prevention and treatment of gastrointestinal diseases, such as can be caused, for example, by microorganisms, bacterial toxins, antiinflammatories, antirheumatics, ethanol, gastric acid or stress situations.—European Patent 544 760 describes combinations of pantoprazole with antibacterially active compounds for controlling the bacterium Helicobacter pylori, which populates the stomach.

DESCRIPTION OF THE INVENTION

Surprisingly, it has now been found that, using proton pump inhibitors as combination components, side effects caused by antibacterially active compounds can be avoided.

The invention therefore relates to the use of proton pump inhibitors as combination therapeutics in the treatment of bacterial diseases which do not effect the gastrointestinal tract using antibacterially active compounds.

The invention further relates to the use of proton pump inhibitors for the production of medicaments for combined use in the treatment of bacterial diseases which do not affect the gastrointestinal tract using antibacterially active compounds.

The invention likewise relates to the combination of proton pump inhibitors with an antibacterially active substance for use in the treatment of bacterial diseases which do not affect the gastrointestinal tract.

The invention furthermore relates to the use of proton pump inhibitors for avoiding side effects which can be caused by antibacterially active substances.

The following compounds, designated by the INN, may be primarily mentioned as proton pump inhibitors: omeprazole, lansoprazole, rabeprazole, leminoprazole, nepaprazole and in particular pantoprazole. The designation "proton pump inhibitors" is intended to mean both the compounds themselves and also their pharmacologically tolerable salts, in particular the salts with bases. Thus the designation "pantoprazole" additionally includes the pharmacologically tolerable salts of pantoprazole, especially the salts with bases, such as are described in European Patent 166 287, in particular the sodium salt.

Examples which may be mentioned of bacterial diseases which do not affect the gastrointestinal tract are infections of the bones and joints, the soft parts, the skin and mucous membranes, the kidneys and the renal pelvis, the efferent ureters, the sex organs and the CNS, in particular infections of the ENT region and of the respiratory tract, such as, for example, bronchitis or pneumonia.

Antibacterially active compounds which may be mentioned are β-lactam antibiotics, for example penicillins (such as benzylpenicillin, phenoxymethylpenicillin, propicillin, azidicillin, dicioxacillin, flucloxacillin, oxacillin, amoxicillin, bacampicillin, ampicillin, meziocillin, piperacillin or aziocillin), cephalosporins (such as cefadroxil, cefaclor, cefalexin, cefalexim, cefuroxim, cefetamet, cefadroxil, ceftibuten, cefpodoxim, cefotetan, cefazolin, cefoperazon, ceftizoxim, ceftaxim, ceftazidim, cefamandol, cefepim, cefoxitin, cefodizim, cefsulodin, ceftriaxon, cefotiam or cefmenoxim) or other β-lactam antibiotics (e.g. aztreonam, loracarbef or meropenem); enzyme inhibitors for example sulbactam, tetracyclines, for example tetracycline, oxytetracycline, minocycline or doxycycline aminoglycosides, for example tobramycin, gentamicin, neomycin, streptomycin, amikacin, netilmicin, paromomycin or spectinomycin; ampherlcols, for example chloramphenicol or thiamphenicol; lincomycins and macrolide antibiotics, for example clindamycin, lincomycin, erythromycin, clarithromycin, spiramycin, roxithromycin or azithromycin; polypeptide antibiotics, for example collstin, polymixin B, teioplanin or vancomycin, gyrase inhibitors, for example norfloxacin, cinoxacin, ciprofloxacin, pipemidic acid, enoxacin, nalidixie acid, pefloxacin, fieroxacin or ofloxacin; nitroimidazoles, for example metronidazole; or other antibiotics, for example fosfomycin or fucidic acid, where these antibacterially active substances are administered on their own or alternatively can be combined with one another.

Side effects of the antibacterially active substances which may be mentioned, which can be avoided by the administration of proton pump inhibitors, are, in particular, atrophic gastritis.

"Combination therapeutic" or "combination" in the sense of the present invention is thus to be understood as meaning that the individual components (i.e. the proton pump inhibitor on the one hand and the antibacterially active substance or active substances on the other hand) can be administered in a manner which is known and customary per se simultaneously (in the form of a combination medicament), more or less at the same time (from separate pack units) or successively (directly one after the other or else with a relatively large time interval).

In the case of administration of the individual components more or less at the same time from separate pack units and in the case of the administration of the individual components which takes place one after the other, it is possible, if desired, to select a different administration form. For example, one component can be orally administered, while the other component is intravenously administered.

The dosage of the antibacterially active substance(s) is carried out in the customary order of magnitude for the respective substance and the respective purpose, in the case of clarithromycin, for example, with a daily dose of 500 to 1000 mg. In the case of the combined us, of a number of antibacterially active substances simultaneously, if appropriate, a lower dosage of the combination components in each case is carried out.

The proton pump inhibitors are administered in the dose customary for them, but preferably in a lower dosage.

Pantoprazole is administered in the customary daily dose of 40 mg. but preferably in a lower dosage (for example 10 to 20 mg/day), in particular in the case of a lower dosage, the proton pump inhibitors can be administered as combination therapeutics in the prophylactic sense in antibiotic therapy.

INVESTIGATION RESULTS

In the investigation on dogs described in detail below, it was possible to show that the atrophic gastritis caused by administration of antibacterially active substances can be avoided by the simultaneous administration of proton pump inhibitors:

MATERIAL AND METHODOLOGY

| Animal material | 22 dogs (beagles; CPB Harlan, Netherlands) |
|---|---|
| Age/weight | male: 12 months/13.8 kg |
| | female: 12.6 months/10.8 kg |
| Number of animals per group | 3m/3f |
| Experimental period | 30 days |
| Recovery time | 4 weeks (group 4) |

TREATMENT

| Group | Substances | Dosage (mg/kg of body weight per day) |
|---|---|---|
| 1 | pantoprazole | 16 |
| 2 | clarithromycin/metronidazole | 75/50 |
| 3 | pantoprazole/clarithromycin/metronidazole | 10/75/50 |
| 4 | as group 3; 4 weeks recovery time | |
| 5 | untreated control | |

| Group | Mucous membrane height (M + F) | Standard archives |
|---|---|---|
| 1 | 1307 | 120 |
| 2 | 868 | 56 |
| 3 | 1233 | 43 |
| 4 | 1142 | 115 |
| 6 | 1086 | 185 |

The conclusion is drawn from this investigation that proton pump inhibitors, such as, for example, pantoprazole, are able to compensate deep-seated and serious morphological alterations to the mucous membrane, which are obviously caused by antibiotics (in this case the combination clarithromycin and metronidazole). Thus proton pump inhibitors should also be able in antibiotic therapy in man to decrease or to prevent the gastrointestinal side effects caused by the antibiotic.

What is claimed is:

1. In a method of treating a bacterial disease which does not affect the gastrointestinal tract and which comprises administering an effective amount of an antibacterially-active compound to a subject afflicted with the bacterial disease, the improvement which comprises administering to the subject a proton pump inhibitor or a pharmacologically-acceptable salt thereof in combination with the antibacterially-active compound.

2. A method of claim 1 wherein the bacterial disease is a bone infection, a joint infection, an infection of soft parts, a skin infection, a mucous membrane infection, a kidney infection, a renal pelvis infection, an efferent ureter infection, a sex organ infection, a CNS infection, an ENT region infection, or a respiratory tract infection.

3. A method of claim 1 wherein the proton pump inhibitor is pantoprazole.

4. A method of claim 1 wherein the proton pump inhibitor is a member selected from the group consisting of omeprazole, lansoprazole, leminoprazole, rabeprazole and nepaprazole.

5. A method of claim 1 wherein the proton pump inhibitor or a pharmacological salt thereof and the antibacterially active compound are administered concurrently or in either order.

6. In the preparation of a medicament composition which has an effective amount of antibacterially-active component for treating a bacterial disease which does not affect the gastrointestinal tract, the improvement which comprises combining a proton pump inhibitor or a pharmacologically-acceptable salt thereof with the antibacterially-active component.

7. A combination of a proton pump inhibitor or a pharmacologically-acceptable salt thereof with an antibacterially-active substance which is used for treating a bacterial disease other than one which affects the gastrointestinal tract.

8. A method of claim 7 wherein the proton pump inhibitor is pantoprazole.

9. A method of claim 7 wherein the proton pump inhibitor is a member selected from the group consisting of omeprazole, lansoprazole, leminoprazole, rabeprazole and nepaprazole.

10. A method of avoiding side effects caused by an antibacterially-active compound which is used for treating a bacterial disease other than one which affects the gastrointestinal tract, which comprises combining a proton pump inhibitor or a pharmaceutically-acceptable salt thereof with the antibacterially-active compound.

11. A method of claim 10 wherein the side effects of the antibacterially-active substance which can be avoided comprise atrophic gastritis.

12. A method of claim 10 wherein the proton pump inhibitor is pantoprazole.

13. A method of claim 10 wherein the proton pump inhibitor is a member selected from the group consisting of omeprazole, lansoprazole, leminoprazole, rabeprazole and nepaprazole.

14. A method of claim 11 wherein the proton pump inhibitor is pantoprazole.

15. A method of avoiding side effects caused by an antibacterially-active compound which is used for treating a bacterial disease other than one which affects the gastrointestinal tract, which comprises administering to a subject in need of such therapy a proton pump inhibitor or a pharmaceutically-acceptable salt thereof in combination with the antibacterially-active compound.

16. A method of claim 15 wherein the side effects of the antibacterially-active substance which can be avoided comprise atrophic gastritis.

17. A method of claim 15 wherein the proton pump inhibitor is pantoprazole.

18. A method of claim 15 wherein the proton pump inhibitor is a member selected from the group consisting of omeprazole, lansoprazole, leminoprazole, rabeprazole and nepaprazole.

19. A method of claim 16 wherein the proton pump inhibitor is pantoprazole.

20. A pharmaceutical composition comprising a) an antibacterially active component for treating a bacterial disease which does not affect the gastrointestinal tract and which has side effects in combination with b) means for counteracting the side effects, which means is a proton pump inhibitor or a pharmaceutically acceptable salt thereof.

* * * * *